(12) United States Patent
Chu et al.

(10) Patent No.: US 7,776,240 B2
(45) Date of Patent: Aug. 17, 2010

(54) INJECTABLE HYDROGEL MICROSPHERES FROM AQUEOUS TWO-PHASE SYSTEM

(75) Inventors: Chih-Chang Chu, Ithaca, NY (US); Xian-Zheng Zhang, Wuhan (CN); Da-Qing Wu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1232 days.

(21) Appl. No.: 10/538,477

(22) PCT Filed: Dec. 4, 2003

(86) PCT No.: PCT/US03/37076
§ 371 (c)(1),
(2), (4) Date: Jun. 7, 2005

(87) PCT Pub. No.: WO2004/066704
PCT Pub. Date: Aug. 12, 2004

(65) Prior Publication Data
US 2006/0073281 A1    Apr. 6, 2006

Related U.S. Application Data

(60) Provisional application No. 60/440,646, filed on Jan. 17, 2003.

(51) Int. Cl.
*B01J 13/02*    (2006.01)
*B01J 13/14*    (2006.01)
*A61K 9/50*    (2006.01)

(52) U.S. Cl. .................. 264/4.1; 264/4.3; 264/4.33; 428/402.2; 428/402.21; 427/213.3; 427/213.36

(58) Field of Classification Search ........... 264/4.1–4.7; 428/402–402.24; 427/213.3–213.36
See application file for complete search history.

(56) References Cited

U.S. PATENT DOCUMENTS

| 4,492,720 | A | * | 1/1985 | Mosier | 427/213.3 |
| 4,822,535 | A | | 4/1989 | Ekman et al. | 264/4.3 |
| 5,596,051 | A | | 1/1997 | Jahns et al. | 526/73 |
| 6,130,318 | A | | 10/2000 | Wild et al. | 530/351 |
| 6,194,531 | B1 | * | 2/2001 | Hatsuda et al. | 526/317.1 |
| 6,596,296 | B1 | | 7/2003 | Nelson et al. | 424/426 |

FOREIGN PATENT DOCUMENTS

| JP | 05255119 A | 10/1993 |
| JP | 11322941 A | 11/1999 |
| WO | WO-9709068 A2 | 3/1997 |
| WO | WO-0109198 A1 | 2/2001 |
| WO | WO 01/92584 A1 | 12/2001 |

OTHER PUBLICATIONS

Cruise, G.M., et al., Biomaterials 19, 1287-1294 (1998).*
Zhang, Xian-Zheng, et al., "Temperature-Sensitive Poly(N-Isopropylacrylamide)/Poly(Ethylene Glycol) Diacrylate Hydrogel Microspheres", Am. J. Drug Deliv., 2005; 3 (1): 1; pp. 1-11.

* cited by examiner

*Primary Examiner*—James Seidleck
*Assistant Examiner*—Saira Haider
(74) *Attorney, Agent, or Firm*—Marjama Muldoon Blasiak & Sullivan LLP

(57) ABSTRACT

Injectable hydrogel microspheres are prepared by forming an emulsion where hydrogel precursors are in a disperse aqueous phase and polymerizing the hydrogel precursors. In a preferred case, the hydrogel precursors are poly(ethylene glycol) diacrylate and N-isopropylacrylamide and the continuous phase of the emulsion is an aqueous solution of dextran and a dextran solubility reducer. The microspheres will load protein, e.g., cytokines, from aqueous solution.

4 Claims, No Drawings

INJECTABLE HYDROGEL MICROSPHERES FROM AQUEOUS TWO-PHASE SYSTEM

CROSS-REFERENCE TO RELATED APPLICATIONS

This application claims the benefit of U.S. Provisional Patent Application No. 60/440,646, filed Jan. 17, 2003.

The invention was made at least in part with United States Government support under United States Department of Commerce Prime Grant Award No. 99-27-07400 pursuant to a subagreement with The National Textile Center. The United States Government has certain rights in the invention.

TECHNICAL FIELD

The invention is directed at injectable hydrogel microspheres and formation thereof, that will load water soluble proteins from aqueous solution and are useful for controlled release of drugs, e.g., water soluble protein drugs.

BACKGROUND OF THE INVENTION

One of the greatest challenges in drug delivery systems is the controlled delivery of protein based drugs due to their short half-life in the circulatory system, low permeability, rapid proteolysis (low stability) and immunogenicity. The use of multiple unit dosage forms, such as polymeric microspheres, greatly reduces absorption differences in patients compared to where single unit dosage forms such as tablets are administered and provides more efficient drug accumulation at target sites in the human body. Many techniques have been proposed for preparation of polymeric microspheres for drug administration. The most commonly used reported techniques involve solvent evaporation or multiple emulsion solvent evaporation. These techniques rely on organic solvents which cause decrease in bioactivity in protein-based drugs and which are generally toxic and therefore require total removal.

The overall survival of patients with oral cancer has remained at about 50% for the last four decades. Cytokine immunotherapy has shown encouraging results in animal models and early clinical tests. However, when cytokines are administered systemically, they exhibit a formidable toxicity profile. While local sustained release of proinflammatory cytokines into tumor microenvironment would be possible by release from hydrogels, loading of known hydrogels with cytokines has required loading from organic solution of cytokine and this results in significant loss of cytokine bioactivity.

Thus there is a need for polymeric microsphere dosage forms which can be formed without the need for use of organic solvents and which will load water soluble protein drugs without inactivation of the drugs.

SUMMARY OF THE INVENTION

It has been discovered herein that injectable hydrogel microspheres can be obtained from hydrogel precursors that are water-soluble and do not require use of organic solvents for their preparation, and that the hydrogel microspheres so obtained, will load water soluble protein from aqueous solution, without inactivation of the protein.

The method of the invention herein is for forming injectable hydrogel microspheres which will load protein from aqueous solution without significant loss of protein activity, to provide sustained release vehicle for active protein.

The method of the invention comprises the steps of:

a) forming an aqueous solution containing as the only hydrogel precursors, hydrogel precursors that are water-soluble, denoted a first aqueous solution, where at least one of the hydrogel precursors functions both as a crosslinker and as a monomer in hydrogel formation, b) admixing with the first aqueous solution a second aqueous solution where the second aqueous solution comprises polymer dissolved in water where the polymer is one that at the concentration of said polymer which is present in the second aqueous solution with any solubility reducer that is present in said second aqueous solution, forms on said admixing an aqueous phase which is immiscible with said first aqueous solution, said second aqueous solution being admixed with the first aqueous solution in a relative amount whereby it will be the continuous phase on formation of an emulsion from the admixture of the first and second aqueous solutions, c) forming an emulsion where the second aqueous solution is the continuous phase and the first aqueous solution is the disperse phase and the disperse phase is constituted of spheres of diameter ranging from 25 to 60 μm as determined by laser diffraction, d) polymerizing the hydrogel precursors of the disperse phase to form hydrogel microspheres, e) collecting the hydrogel microspheres.

Another embodiment of the invention is directed at injectable hydrogel microspheres which can be loaded with cytokine from aqueous solution. The injectability of the hydrogels is advantageous for ease of administration.

The term "hydrogel" is used herein to mean a polymeric material which exhibits the ability to swell in water and to retain a significant portion of water within its structure without dissolution.

The term "hydrogel precursor" is used herein to mean water soluble composition that is polymerizable in aqueous solution to form a hydrogel.

The term "microsphere" is used herein to mean spherical particles having diameters ranging from 1 to 200 or 300 μm unless otherwise defined herein.

DETAILED DESCRIPTION

Hydrogel precursor that functions as both as a crosslinker and as a monomer in hydrogel formation is preferably poly(ethylene glycol diacrylate) (sometimes referred to herein as PEG-DA) where the poly(ethylene glycol) has a weight average molecular weight ranging from 2,000 to 35,000. The PEG-DA is preferably prepared from poly(ethylene glycol) diol by reaction thereof with acryloyl chloride to form acrylate diesters of poly(ethylene glycol) as described in Cruise, G. M., et al, Biomaterials 19, 1287-1294 (1998). The poly(ethylene glycol) diol starting material is commercially available.

Other hydrogel precursor preferably also included in the first aqueous solution is N-isopropylacrylamide (sometimes referred to as NIPAAm). The NIPAAm furnishes temperature sensitivity to the resulting hydrogel whereby the resulting hydrogel loses water and any protein dissolved therein when a lower critical solution temperature is exceeded. The term "lower critical solution temperature" (sometimes referred to herein as "LCST") is the endothermic peak determined by a thermogram taken on hydrogel microsphere and is the temperature above which the hydrogel collapses and the volume of the hydrogel shrinks dramatically. The hydrogels herein from NIPAAm and PEG-DA have a LCST of about 29° C.

The term "temperature sensitivity" is used herein to mean change of temperature causing shrinkage and water loss.

For first aqueous solutions containing NIPAAm and PEG-DA, the concentration for the NIPAAm in the first aqueous solution ranges, for example, from 5 to 25% (wt/vol %), and the concentration range for the PEG-DA in the first aqueous solution, ranges, for example, from 2 to 50% (wt/vol %).

The polymer for the second aqueous solution is water soluble and as indicated above is one that at the concentration of the polymer which is present in the second aqueous solution with any solubility reducer that is present in the second aqueous solution, forms on the admixing of step (b) an aqueous phase which is immiscible with said first aqueous solution. Water soluble polysaccharides are preferred for the polymer of the second aqueous solution. Dextrans having weight average molecular weight ranging from about 40,000 to 80,000 are very preferred.

Other water-soluble polysaccharides, such as chitosan, starch, algal fucoidan, cellulose, pectins, heparin, cashew-nut tree gum and glycogen can substitute for the dextran. Other polymers besides polysaccharides for the second aqueous solution, are, for example, polyelectrolyes, such as polyethyenimine or polyacrylic acid; poly(vinyl pyrrolidone); copolymer of ethylene oxide and propylene oxide; and mixtures of sodium caseintae and sodium alginate.

When dextran is used as the polymer of the second aqueous solution, compound can be added to the second aqueous solution to reduce the solubility of dextran in water, to foster the formation of a two-phase aqueous system on the admixing of step (b) due to polymer-polymer insolubility, i.e., to "salt out" the PEG-DA and NIPAAm from the dextran and facilitate the immiscibility between the two aqueous phases without the need for emulsifying agents or stabilizers. A preferred compound for this purpose is $MgSO_4$. Other salts such as KCl and magnesium phosphate can substitute for the $MgSO_4$.

For the dextran and $MgSO_4$ in the second aqueous solution, the concentration of dextran in the solution can range, for example, from 10 to 50% (wt/vol %) and the concentration of $MgSO_4$ can range, for example, from 10 to 60% wt/vol %).

In step (b) the first and second aqueous solutions are admixed in relative amounts so that the second aqueous solution constitutes the continuous phase and the first aqueous solution constitutes the disperse phase on formation of an emulsion in step (c).

Formation of an emulsion is step (c), can be carried out by vigorous mixing, for example, for 15 minutes to 2 hours whereby a two-phase water-in-water emulsion system forms and stabilizes after no mixing, for example, for 10 minutes to 1 hour. The disperse phase is constituted of spheres of first aqueous solution that range in diameter from 25 to 60 μm, as determined by a laser diffraction method. As indicated above, no emulsifying agent needs to be present; emulsifying agent is preferably not present.

The polymerization of step (d) is readily carried out by adding initiator to the formed emulsion. For polymerization and crosslinking of PEG-DA and NIPAAm, an initiator system of ammonium persulfate and N,N,N',N'-tetramethylethylenediamine is preferred. Other initiator systems include, for example, ammonium peroxydisulfate and sodium busulfite, potassium persulfate and sodium bisulfite, ammonium peroxydisulfite and ascorbic acid, potassium persulfate and ascorbic acid and the system of hydrogen peroxide and $Fe^{2+}$.

Polymerization and crosslinking reaction can be carried out 15 minutes to 24 hours at 15 to 45° C.

The collection of step (e) can be carried out by decanting of continuous phase and purification by multiple centrifugations with distilled water.

Drying of the collected hydrogel microspheres is preferably carried out in a way to maintain the shape of the microspheres and keep them separate from one another. This can be accomplished, for example, by placing aqueous solution containing water swollen microspheres on a glass slide, removing surplus water with moist filter paper, and drying in air, e.g. for 15 to 30 hours or by freeze drying.

The dried microspheres have a freeze dried diameter ranging from 10 to 35 μm as determined by using a scanning electron microscope.

Loading of water soluble protein, e.g., cytokine such as interkeukin-2, is carried out, for example, by immersing dried hydrogel microspheres in a soluble protein loaded phosphate-buffered solution, for 1 to 4 days.

We turn now to the embodiment of the invention directed to injectable microspheres which can be loaded with cytokine from aqueous solution. The injectable microspheres are preferably hydrogel microspheres formed by polymerizing of poly(ethylene glycol) diacrylate (where the polyethylene glycol has a weight average molecular weight ranging from 2,000 to 35.000) and N-isopropylacrylamide and are prepared as described above and loaded with cytokine as described above.

The injectable hydrogels have a temperature sensitive release pattern, i.e., increase in temperature causes shrinking and water loss.

The weight average molecular weights herein are determined by gel permeation chromatography versus manodispersed polystyrene standards.

The invention is supported by experiments and results and conclusions from those set forth in manuscript titled PNIPAAm/PEG-DA hydrogel microsphere synthesized in an aqueous two-phase system, which is part of U.S. Provisional Patent Application No. 60/440,646. the whole of U.S. Provisional Patent Application No. 60/440,646 is incorporated herein by reference.

The invention is illustrated by the following working examples.

EXAMPLE I

Poly(ethylene glycol) (weight average molecular weight of 3600) diacrylate (PEG-DA) was prepared by the method of Cruise, G. M., et al, Biomaterials 19, 1287-1294 (1998).

PEG-DA (0.35 g) and N-isopropylacrylamide (NIPAAm, 0.75 g) were dissolved in distilled water (5.0 ml) to form an aqueous solution. Then dextran (weight average molecular weight of 43,000, 3.0 g) and anhydrous magnesium sulfate ($MgSO_4$, 3.0 g) were dissolved in distilled water (10 ml) to form a second aqueous solution. The two aqueous solutions were vigorously mixed for 30 minutes at a stirring rate of 800 rpm. Phase separation took place and the resulting water-in-water emulsion system was allowed to stabilize for 20 minutes. Subsequently ammonium peroxydisulfate (150 μl, 5.0 wt % water solution) and N,N,N',N'-tetramethylethylenediamine (100 μl) were added to initiate the polymerization/crosslinking reaction. The reaction was carried out without stirring for 30 minutes at 22° C. to polymerize the acryloyl moieties in the NIPAAm and PEG-DA. Finally, the resulting hydrogel microspheres were collected and purified by multiple centrifugations with distilled water. Drying was carried out by drying in air as described above.

For determination of controlled release function of the hydrogel microspheres, bovine serum albumin (BSA) was selected as a model high-molecular mass protein drug.

Dried hydrogel microspheres were immersed into a BSA loaded (8.0 g BSA and 25 ml phosphate buffered saline)

phosphate buffered solution (PBS, pH 7.4) at 22° C. for two days whereby BSA was loaded into the hydrogel microspheres via equilibrium partition. The swollen BSA loaded hydrogel microspheres were then used for a subsequent BSA release study. The release experiment of BSA from the hydrogel microspheres was conducted in pH 7.4 phosphate buffered saline (PBS) at temperatures below (22° C.) or above (37° C.) its LCST. The release profile was monitored by UV spectroscopy at an absorbance of 277 μm. At 22° C., nearly 60% of BSA was released from hydrogel microspheres in 12 hours, whereas 40% BSA was released from hydrogel microspheres at 37° C., demonstrating that drug release can be controlled by change in the environmental temperature. The experiment shows sustained release since all of the BSA was not released during the first 24 hours. Extrapolation of the results indicates that release of BSA will be sustained for about one week or longer.

EXAMPLE II

Poly(ethylene glycol) diacrylate (PEG-DA) was prepared using poly(ethylene glycol) diol of weight average molecular weight of 8,000 by the method of Cruise, G. M., et al. Biomaterials 19, 1287-1294 (1998). In brief, 25 g poly(ethylene glycol) diol (8,000) denoted PEG diol, was dissolved in 50 ml of anhydrous benzene to form a solution denoted PEG solution. Triethylamine (four fold molar excess based on PEG diol end groups) was added to the PEG solution at room temperature and then acryloyl chloride (four fold molar excess based on PEG diol end groups) was added dropwise to the PEG solution to form acrylate diesters of PEG. The mixture was stirred overnight at 35° C. under dry $N_2$. The insoluble triethylamine salts produced during the reaction were filtered out and the PEG diacrylate (PEG-DA) product was precipitated by the addition of 1.0 L of chilled diethyl ether (4° C.). The precipitate PEG-DA was collected and purified by recrystallazation in anhydrous benzene/chilled diethyl ether twice. The purified PEG-DA was collected and dried overnight under vacuum at 40° C.

The PEG-DA (8,000, 0.35 g) and N-isopropylacrylamide (NIPAAm, 0.75 g) were dissolved in 5.0 mL distilled water to form an aqueous phase. Due to the presence of diacrylate groups, PEG-DA acted as the crosslinker as well as the precursor during the subsequent polymerization/crosslinking reactions. Then, dextran (weight average molecular weight of 66,000, 3.0 g) and anhydrous $MgSO_4$ (3.0 g) were dissolved in 10 mL distilled water to form another aqueous phase. Here, the anhydrous $MgSO_4$ was used to salt out of PEG-DA and NIPAAm from the dextran (i.e., increasing immiscibility between the two aqueous systems: dextran and NIPAAm/PEG-DA) in order to facilitate the formation of two immiscible aqueous phases as mentioned above. These two aqueous solutions were vigorously mixed for 60 min at a stirring rate of 800 rpm. Phase separation took place and the resulting water-in-water emulsion system was allowed to stabilize for 30 min. Subsequently, 0.5 mL ammonium persulfate solution (50 mg/mL) and 0.1 mL N,N, N',N'-tetramethylene diamine were added.

Without stirring, the mixture was placed at room temperature for 12 hr for the polymerization/crosslinking of the acryloyl moieties in the NIPAAm and PEG-DA phase. The resulting crosslinked PNIPAAm/PEG-DA microspheres were purified by multiple centrifugation and washing steps with distilled water. A suspension of swollen microspheres in water at a concentration of 10 wt % at room temperature appeared translucent.

The concentrated equilibrium swollen microspheres were dried in a Vertis Freeze Drier (Gardiner, N.Y.) under vacuum at −42° C. for at least 3 days until all the water sublimed.

The yield of freeze dried microspheres from precursor was about 54%.

The size of the swollen hydrogel microspheres was determined by laser diffraction as follows: Freeze dried microspheres were suspended in HPLC grade water (5% vol), then sonication was carried out to achieve a homogenous suspension, followed by measuring particle size using a particle size analyzer (Particle Size Analyzer 2010, Brinkman Instruments, Inc., NY, USA) which functions using laser diffraction. Nearly 60% of the swollen microspheres were determined to have a diameter of about 50 μm.

Freeze dried hydrogel microspheres were examined by using a scanning electron microscope (Hitachi S4500 SEM, Mountain View, Calif., USA). Before SEM observation, the microspheres were fixed on aluminum stubs and coated with gold. The SEM images indicated size of about 25 μm in diameter.

The discrepancy in size between the diameter measured by the particle size analyzer and by SEM measurement was attributed to the difference in measuring hydrodynamic diameter in one case and non-hydrodynamic diameter in the other. It was found to be impossible to use SEM to observe hydrogel microspheres in their natural swollen state because of the high vacuum needed for SEM observations. Use of environmental scanning electron microscope (ESEM, Phillips ElectroScan 220) and preparing samples by casting a drop of microsphere suspension onto a microscopy stub for direct observation at room temperature showed a hydrated microsphere size of about 25 μm in diameter which is consistent with the size obtained on freeze dried particles by SEM observation.

The LCST behavior of the hydrogels was examined using differential scanning calorimetry (DSC) (TA 2920 Modulated DSC, TA Instruments, Inc, DE, USA). Each sample was immersed in distilled water at room temperature to reach equilibriumn state before the DSC measurement. About 10 mg equilibrium swollen sample was placed inside a hermetic aluminum pan, which was then sealed tightly with a hermetic aluminum lid. Thermal analysis was performed from 15 to 55° C. on swollen microsphere samples at a heating rate of 3° C./min under dry nitrogen (40 mL/min). An LCST of about 29.1° C. was observed. The existence of the LCST shows that the hydrogel microspheres are temperature sensitive, i.e., increase in temperature causes shrinking and water loss.

Equilibrium swelling ratio at room temperature (22° C.) was determined as follows:

A predetermined amount of the freeze dried microsphere sample was placed within a cylindrical plastic tube (45 ml) and the lid of the tube was closed and the weight was measured. Water (about 30 ml) was added to the tube and the microspheres were allowed to swell at room temperature for 12 hrs with continuous shaking. The swollen hydrogel microspheres were centrifuged and concentrated. After removing the upper transparent liquid with a pipette carefully, the collected microspheres were weighed rapidly and placed in a plastic tube. After that, the same volume fresh water was added back to the concentrated microspheres under shaking. The tube was incubated at room temperature for 8 hrs and the swollen hydrogel microspheres were then centrifuged and concentrated again. This swelling-centrifugation-weighing process was repeated several times until the weight of the microspheres became constant, which means the hydrogel microspheres reached the equilibrium swelling state in the solvent. The average value among three equilibrium swellings for each sample were taken, and the swelling ratio was calculated as follows, $$\text{Swelling ratio} = (W_s - W_d)/W_d$$

Where $W_s$ is the weight of swollen hydrogel microspheres and $W_d$ is the weight of dry microspheres. The swelling ratio determined is 20±4.

A model drug is incorporated below. Swelling ratio relates to the rate and amount of impregnated drug released. The larger the swelling ratio, the faster the rate of release and the larger the amount of drug that is released is believed to be the normal case. The swelling ratio determined here indicates sustained release utility for the hydrogel microspheres.

Bovine serum albumin (BSA) was chosen as a model protein drug for impregnation into the hydrogel microspheres.

A pre-loading method was used to incorporate BSA before formulating hydrogel microspheres. A fixed amount of BSA (3.0 wt. % of the polymer precursors) was added to the precursor solution (i.e. PNIPAAm/PEG-DA aqueous phase). This BSA-loaded PNIPAAm/PEG-DA solution was then added into dextran/$M_g$ $SO_4$ solution for the preparation of hydrogel microspheres. After the polymerization and crosslinking, BSA loaded PNIPAAm/PEG-DA hydrogel microspheres were quickly purified by centrifugation and washing with distilled water within 5 hrs.

The drug loaded hydrogel microspheres (10 mg) were then placed inside a 2.0 mL vial containing 1.5 mL phosphate-buffered solution (PBS) (0.1 M, pH 7.4). The vial was placed in an incubator at a predetermined temperature (either room temperature, i.e., 22° C., or 37° C.). At a predetermined immersion period, the vial was centrifuged for 5 mins at 10,000 rpm and 1.0 mL of the supernant was removed and replaced by fresh PBS. The BSA content of the supernatant was measured by a Perkin Elmer Lambda 2 UV/VIS spectrometer (Norwalk, Conn.) at 277 μm and the concentration of BSA released was calculated from a BSA standard calibration curve. All release studies were carried out in duplicate. The results were presented in terms of cumulative release as a function of time, according to following equation:

$$\text{Cumulative amount released (\%)} \ (M_t/M_o) \times 100$$

where $M_t$ is the amount of BSA released from the hydrogel microspheres at time t, and $M_o$ is the initial amount of BSA loaded in the hydrogel microsphere.

The cumulative amounts of BSA released from hydrogel microspheres over time at 22° C. (below LCST) and 37° C. (above LCST) were determined. Regardless of temperature, the hydrogels showed a biphasic modulation characterized by an initial relatively rapid release period, followed by a slower release period. The release rate and extent of release of BSA at 37° C. was slower and lower than those at 22° C. For example, within the first 8 hrs, the cumulative BSA released was about 21% at 22° C. and 13% at 37° C. The cumulative BSA release during the 22-day study period was 60% at 22° C. versus 52% at 37° C. While not wishing to be bound by speculation, it is posited that the less release at 37° C. was attributed to entrapping of BSA in a collapsed matrix above the LCST.

The experiment showed a difference in release rate because of difference in external temperature.

Variations

Variations will be obvious to those skilled in the art. Thus, the scope of the invention is defined by the claims.

What is claimed is:

1. A method for forming hydrogel microspheres which will load a protein from aqueous solution, comprising the steps of
   a) forming an aqueous solution of hydrogel precursors that are water soluble, denoted a first aqueous solution, where at least one of the hydrogel precursors of the first aqueous solution functions both as a crosslinker and as a monomer in hydrogel formation and is polyethylene glycol diacrylate where the poly (ethylene glycol) has a weight average molecular weight ranging from 2,000 to 35,000, and a second hydrogel precursor of the first aqueous solution is N-isopropylacrylamide,
   b) admixing the first aqueous solution a second aqueous solution where the second aqueous solution comprises polymer dissolved in water where the polymer is one that the concentration of said polymer which is present with any solubility reducer that is present, forms on said admixing an aqueous phase which is immiscible with said first aqueous solution, said second aqueous solution being admixed with the first aqueous solution in a relative amount whereby it will be the continuous phase on formation of an emulsion from the admixture of the first and second aqueous solutions,
   c) forming an emulsion where the second aqueous solution is the continuous phase and the first aqueous solution is the disperse phase and the disperse phase is constituted of spheres of diameter ranging from 25 to 60 μm as measured by laser diffraction,
   d) polymerizing the hydrogel precursors of the disperse phase to form hydrogel microspheres,
   e) collecting the hydrogel microspheres.

2. The method of claim 1 where the polymer of the second aqueous solution is a water-soluble polysaccharide.

3. The method of claim 2 where the polymer of the second aqueous solution is dextran having a weight average molecular weight ranging from 40,000 to 80,000.

4. The method of claim 3 where the second aqueous solution contains a constituent to reduce the solubility of the dextran in water so that a two-phase aqueous system can be formed on the admixture of step (b).

* * * * *